United States Patent [19]

Duckworth et al.

[11] Patent Number: 4,837,007
[45] Date of Patent: Jun. 6, 1989

[54] FLUORIDATING ORAL CAVITY

[75] Inventors: Ralph M. Duckworth, Tarporley; Andrew M. Murray, South Wirral, both of England

[73] Assignee: Lever Brothers Company, New York, N.Y.

[21] Appl. No.: 938,218

[22] Filed: Dec. 5, 1986

[30] Foreign Application Priority Data

Dec. 11, 1985 [GB] United Kingdom ............... 8530493
Mar. 20, 1986 [GB] United Kingdom ............... 8606909

[51] Int. Cl.$^4$ ............................................. A61K 7/18
[52] U.S. Cl. ........................................ 424/52; 424/49; 424/54; 514/901
[58] Field of Search ................. 424/49, 52, 54; 514/901

[56] References Cited

U.S. PATENT DOCUMENTS

| | | | |
|---|---|---|---|
| 3,489,686 | 1/1970 | Parran | 252/106 |
| 3,580,853 | 5/1971 | Parran | 252/152 |
| 4,110,083 | 8/1978 | Benedict | 424/49 |
| 4,157,387 | 6/1979 | Benedict | 424/49 |
| 4,411,889 | 10/1983 | Caslavsky et al. | 424/151 |
| 4,428,930 | 1/1984 | Chang | 424/49 |

FOREIGN PATENT DOCUMENTS

| | | |
|---|---|---|
| 601116 | 1/1985 | Japan . |
| 2021949 | 12/1979 | United Kingdom . |
| 2118835 | 11/1983 | United Kingdom . |
| 2126081 | 3/1984 | United Kingdom . |

OTHER PUBLICATIONS

"Chemical Abstracts", vol. 87, No. 4, 25th Jul. 1977, p. 379, Abstract No. 28943e, Columbus, Ohio; O. R. Tarwater et al.: Controlled Release of Fluoride from Hydrogels for Dental Applications, & Polym. Prepr., Am. Chem. Soc. Div. Polym. Chem. 1975, 16(2), 382–386.
"Chemical Abstracts", vol. 70, No. 9, 34d Mar. 1969, p. 250, Abstract No. 40646s, Columbus, Ohio; & S.A. 67 06, 957, 10-04-1968.

*Primary Examiner*—Howard E. Schain
*Assistant Examiner*—F. T. Maezil
*Attorney, Agent, or Firm*—Milton L. Honig

[57] ABSTRACT

The disclosure concerns an oral hygiene product which provides in the mouth a reservoir for the slow release of a therapeutic agent, such as fluoride ions. The product comprises two compositions which are mixed in the mouth or before introduction into the mouth. One composition comprises an aqueous suspension of particles which slowly release the therapeutic agent in salvia. The other composition comprises an aqueous solution of a cationic polymer.

8 Claims, No Drawings

FLUORIDATING ORAL CAVITY

This invention relates to oral products, more particularly oral hygiene products which comprise a therapeutic agent. The invention will be described with particular reference to its application to the use of fluorine-containing therapeutic agents for combating dental caries. However, it is evident that the invention is in principle applicable to the delivery in the oral cavity of other therapeutic agents.

It is well known to include water-soluble fluorine-containing salts, for example sodium fluoride or sodium monofluorophosphate, in oral products, especially mouthwashes and toothpastes, and that by regular use of such products the incidence of dental caries can be reduced. It is believed that the fluoride ion or monofluorophosphate ion, interacts with the tooth substance and increases its resistance to acid attack. However, the opportunity for this efficacious interaction to occur is short-lived because the oral fluoride level falls off rapidly after use of a mouthwash or toothpaste.

Evidence is given by Fejerskov et al (Acta Odontol. Scand., 1981, 39, 241-249) that fluoride, even in low concentrations, is necessary in the oral fluids to obtain maximum caries inhibition concluding that continuous or frequent supplementation of fluoride to oral fluids is mandatory particularly in cases of increased cariogenic challenge at any age.

Attempts have been made to provide means for maintaining a certain concentration of fluoride ions in the mouth over a longer period. These have included proposals for locating a fluoride ion source in the mouth, for example as part of an orthodontic appliance. More recently, Williams et al, Journal of Pedodontics, Spring 1982, 218-228, have disclosed adhering fluoride-containing microcapsules to teeth with guar gum to provide a sustained release source of fluoride. Spooner et al, Int. J Pharmaceutics, 15, 177-184, 1983 describe a device located at a demineralised enamel surface for the sustained release of fluoride ions which device comprises a supply of particles of calcium fluoride contained within a membrane. Ogaard et al, Caries Res., 17, 520-524, 1983 postulate that calcium fluoride formed in outer layers of tooth enamel by treatment with an aqueous solution of sodium fluoride might well serve as a significant reservoir of fluoride and may be of prime importance concerning the cariostatic effect of the retained fluoride.

It is an object of the invention to provide an oral hygiene product adapted to result in use in a sustained therapeutic activity in the oral fluid by prolonged release of a therapeutic agent, especially fluoride ions, from a particulate reservoir.

According to one aspect of the present invention, there is provided an oral hygiene product which comprises, as a combined preparation, a first composition and a second composition for admixing in the mouth or for admixing prior to introduction into the mouth, wherein:

the first composition comprises an aqueous suspension of particles which slowly release a therapeutic agent in saliva, and the second composition comprises an aqueous solution of a cationic polymer.

The above oral product according to the invention is in part based on the concept of providing a sustained therapeutic activity in the oral fluid through the release of therapeutic agent from particles which are attached to oral surfaces. In our research we have found that the presence of saliva severely interferes with the deposition of particles onto the oral surfaces but it has been found that by bringing the particles into contact with a solution of a cationic polymer prior to or simultaneously with their introduction into the mouth then the inhibiting effect of the saliva can be overcome and thereby an efficacious deposition of particles capable of releasing a therapeutic agent, especially fluoride ions, effected.

The surface charge characteristics of the particles capable of releasing a therapeutic agent may be anionic, cationic, non-ionic or amphoteric.

The particles constituting a fluoride ion source are preferably particles of magnesium fluoride but other slightly water-soluble salts can also be used, such as calcium fluoride, strontium fluoride and the mixed salt neighborite ($NaMgF_3$). Alternative particulate fluoride ion sources could be, for example, polymeric latices which release fluoride.

Fluoride ion-releasing particles suitably have a size of from 0.01 to 5 microns. The rate of release of fluoride ions is believed to be related to particle size and it is considered that particles in this range provide an optimum release rate. The preferred range is 0.05 to 0.5 microns.

It is required that the particles of the therapeutic material should not release active molecules significantly during storage of the product but should release material to a substantial extent in the mouth in the time between one product application and the next, say in about 2 to 24 hours. For example, dissolving particles should therefore have an appropriate thermodynamic solubility constant. For a divalent metal fluoride such as magnesium fluoride the solubility constant ($K_{sp}$) will generally be between about $5 \times 10^{-19}$ and about $6.5 \times 10^{-5}$ mol$^3$ dm$^{-9}$.

The actual concentration of fluorine in a fluorine-containing product according to the invention will be within conventional limits, usually determined by local legislation. Thus the fluorine level will generally not exceed about 1500 ppm but for the purpose of this invention this limit is not critical.

The cationic polymer serves to enhance the substantivity to oral surfaces of the particles capable of releasing the therapeutic agent. A wide range of cationic polymers are commercially available. Examples of suitable polymers are those based on acrylamide and a cationic monomer, such as those available commercially under the name FLOC AID from National Adhesives and Resins Limited, Great Britain, or under the name RETEN from Hercules Inc. U.S.A. Particular examples of such resins are FLOC AID 305 and RETEN 220. Further examples of suitable polymers are the cationic guar derivatives such as those sold under the name JAGUAR by Celanese-Stein Hall, U.S.A.

The cationic polymers desirably have a cationic charge density of at least 0.0005. Charge density refers to the ratio of the number of charges on a polymer unit to the molecular weight of said polymer unit. The polymers generally have a molecular weight of at least about 10,000 and usually at least 100,000.

The concentration of the cationic polymer in the combined preparation is suitably about 3 to 600 ppm, preferably 10 to 300 ppm.

In use the product may be employed as in the manner of an oral rinse. The two compositions may be first mixed together or they may be taken into the mouth separately where they become mixed.

Either or both of the compositions desirably contain a flavouring agent. Conventional flavours for oral products may be used.

The compositions may also comprise other ingredients such that the combined composition is in the form of a mouthwash. Thus, one or both of the compositions may comprise ethanol, sorbitol or glycerine, antibacterial agent, sweeteners, emulsifying agent, water soluble fluoride.

According to a second aspect of the invention there is provided an oral hygiene product in the form of a mouthwash which comprises a suspension in an aqueous or aqueous alcoholic medium of positively charged particles which slowly release a therapeutic agent, preferably magnesium fluoride particles, the said medium containing dissolved therein the cationic polymer.

The composition of the invention may also be in the form of a toothpaste. One form of dispenser suitable for a toothpaste product according to this invention is one in which two or more materials are combined at the time of usage and applied to the bristles of a toothbrush. Examples of such dispensers are described in US-A-No. 3 290 422 (Michel to American Can Co.), GB-A-No. 1 335 082 (Blendax-Werke) and GB-A-No. 1 491 053 (Procter & Gamble). In formulating a toothpaste compositon comprising two or more parts it is required that prior to dispensing, contact should be avoided between ingredients of opposite charge, for example the cationic polymer and an anionic surfactant, if utilised.

Through the use of an oral hygiene product of this invention fluoride-ion releasing particles can be made to adhere to and be retained on oral surfaces and thereby act as fluoride reservoirs releasing fluoride ions at a controlled rate into saliva so that fluoride becomes available to all the tooth surfaces at any time. This constant bioavailability of fluoride acts to give a measure of all day protection against dental caries. Regular use of the oral hygiene product of the invention will therefore help to maintain the teeth in a more healthy state.

The following are examples of oral hygiene products in accordance with the present invention. Percentages are by weight.

EXAMPLE 1

The following is an example of a two-part mouthwash product.

|  | % |
|---|---|
| First composition |  |
| Particles of $MgF_2$ | 0.2 |
| Water | to 100.0 |
| Second composition |  |
| RETEN 220 | 0.01 |
| Water | to 100.00 |

The first and second compositions are mixed in equal proportions before use.

The particles of magnesium fluoride had an average particle size of about 0.1 micron, the particle diameters ranging from about 0.05 micron to about 0.2 micron.

RETEN 220 is a cationic high molecular weight acrylamide-based copolymer. Solutions of solid content 0.5% and 1.0% have viscosities of, respectively, about 325 and 750 centipoises (determined at 20° C., Brookfield model LVF viscometer with spindle speed of 60 rpm). The copolymer has an approximate weight average molecular weight of 2,500,000. The cationic charge density is approximately 0.001. The ratio of quaternised dimethylaminoethylmethacrylate groups to acrylamide groups is approximately 1:12.

The first and second compositions were mixed together with human saliva in the proportions 10 parts mouthwash to 1 part whole human saliva to simulate oral conditions. Particle deposition from this suspension onto a suitable substrate (e.g. a saliva coated glass slide) was about 100 times greater than that obtained in a similar experiment in which the cationic polymer was omitted.

EXAMPLE 2

A two-part mouthwash product was made comprising a first composition and a second composition prepared from the ingredients indicated below.

|  | % |
|---|---|
| First composition |  |
| Particles of $MgF_2$ | 0.082 |
| Water | to 100.000 |
| Second composition |  |
| FLOC AID 305 | 0.06 |
| Water | to 100.00 |

The first composition (5 ml) was mixed with the second composition (5 ml) before use to give a mouthwash containing 250 ppm F.

The particles of magnesium fluoride had an average particle diameter of 0.06 $\mu$m, the diameters ranging from about 0.04 $\mu$m to about 0.08 $\mu$m.

FLOC AID 305 is a cationic acrylamide-based copolymer having an approximate weight average molecular weight of 2,000,000. The ratio of quaternised dimethylaminoethylmethacrylate groups to acrylamide groups is approximately 1:5. The cationic charge density of this polymer is about 0.002.

The mouthwash (10 ml) was held in the mouth for one minute and then expectorated. Saliva samples were collected at regular intervals for several hours after application of the mouthwash. The saliva samples were buffered to pH5 by adding 10% by weight of a buffer known in the art as a total ionic strength adjusted buffer, which was composed of sodium hydroxide (10%), acetic acid (28.5%), trans-1,2-diaminocyclohexane-N,N,N',N'-tetraacetic acid (2%) and water (to 100%).

The fluoride ion activities of the buffered saliva samples were measured using a fluoride ion specific electrode (Orion 94-09). Measurements were either made within 5 minutes, to obtain free fluoride ion concentrations, or after two days to obtain the total fluoride concentration by allowing for dissolution of the $MgF_2$ particles suspended in the saliva.

A similar procedure was followed using a control mouthwash consisting of an aqueous solution containing 0.055% NaF to give a fluoride concentration of 250 ppm.

The results are given in the following table.

TABLE

| Mouthwash | | Salivary Fluoride (ppm) Time (mins): | | | |
|---|---|---|---|---|---|
| | | 90 | 120 | 150 | 180 |
| Example 2 | free $F^-$ | 0.72 | 0.35 | 0.31 | 0.21 |
| | total F | 13.57 | 4.30 | 2.34 | 1.56 |

TABLE-continued

| Mouthwash | Salivary Fluoride (ppm) Time (mins): | | | |
|---|---|---|---|---|
| | 90 | 120 | 150 | 180 |
| Control | 0.20 | 0.14 | 0.11 | 0.08 |

The results show that the mouthwash of the invention gives substantially elevated salivary fluoride levels of both total fluoride and free fluoride relative to the sodium fluoride control mouthwash.

EXAMPLE 3

A two-part mouthwash product was made as indicated in Example 2 save that the second composition contained 0.02% FLOC AID 305.

The procedure as described in Example 2 was then followed. The salivary fluoride levels resulting from use of the mouthwash of this example were as follows:

| Time (mins) | Salivary Fluoride (ppm) |
|---|---|
| 90 | 15.25 |
| 120 | 4.54 |
| 150 | 2.90 |
| 180 | 1.04 |

These results taken with those of Example 2 show that when reducing the concentration of the polymer in the mouthwash from 300 ppm (Example 2) to 100 ppm, there is little change in the total fluoride content of the saliva.

EXAMPLE 4

A mouthwash product was made comprising a first composition and a second composition prepared from the following ingredients:

| | % |
|---|---|
| First composition | |
| Particles of MgF$_2$* | 0.15 |
| Water | to 100.00 |
| Second composition | |
| RETEN 220 | 0.06 |
| Water | to 100.00 |

*as in Example 1.

The first composition (5 ml) was mixed with the second composition (5 ml) to give a mouthwash containing 440 ppm F.

A control mouthwash was also prepared consisting of an aqueous solution of NaF having a fluoride concentration of 440 ppm F.

The procedure as described in Example 2 was then followed. The salivary fluoride levels resulting from use of the mouthwash of the invention and the control mouthwash, respectively, were as follows:

| Time (mins) | Salivary Fluoride (ppm) | |
|---|---|---|
| | Example 4 Mouthwash | Control Mouthwash |
| 60 | 19.39 | 0.61 |
| 120 | 7.13 | 0.22 |
| 180 | 3.11 | 0.13 |
| 240 | 1.71 | 0.09 |

EXAMPLE 5

A mouthwash product comprising a water-soluble fluoride (sodium fluoride) is illustrated by this Example.

| | % |
|---|---|
| First composition | |
| Particles of MgF$_2$ | 0.10 |
| NaF | 0.14 |
| Water | to 100.00 |
| Second composition | |
| RETEN 220 | 0.01 |
| Water | to 100.00 |

The first and second compositions are mixed in equal proportions before use.

EXAMPLE 6

The following is a further example of a two-part mouthwash product.

| | % |
|---|---|
| First composition | |
| Particles of MgF$_2$ | 0.20 |
| Na$_2$HPO$_4$ | 0.14 |
| Water | to 100.00 |
| Second composition | |
| RETEN 220 | 0.01 |
| Water | to 100.00 |

The first and seocnd compositions are mixed in equal proportions before use.

The effect of the Na$_2$HPO$_4$ in the first composition is to reverse the charge on the particles of the magnesium fluoride. The presence of the Na$_2$HPO$_4$ tends to improve the storage stability of the composition.

EXAMPLE 7

A further example of a two-part mouthwash composition is the following.

| | % |
|---|---|
| First composition | |
| Particles of fluoropolymer A | 2.5 |
| Glycerol | to 100.0 |
| Second composition | |
| RETEN 220 | 0.0067 |
| Water | to 100.0 |

One part of the first composition is mixed with 3 parts of the second composition before use. After deposition in the mouth the particles of the fluoropolymer hydrolyse to release fluoride ions.

The fluoropolymer A is a poly(methacryloxypropyl difluorohydroxysilane) stabilised by grafted poly(vinyl methyl ether) and was prepared in the form of the first composition as follows.

Poly(vinyl methyl ether) (8.0 g) was dissolved in dry cyclohexane (180 cc) contained in a 250 ml flask equipped with stirrer, condenser and nitrogen blanket facility. A portion of the cyclohexane (25 cc) was distilled off to remove traces of moisture, and the remainder was purged with dry nitrogen. Azobisisobutyronitrile (0.05 g), recrystallised from ethanol, was dissolved in the solution. Methacryloxypropyl difluorohydroxysilane (25 g) dissolved in dry cyclohexane (25 cc) was added dropwise to the stirred reactor at 85° C. The first portion of monomer solution (about 2 cc) was added very slowly over a two-hour period, so that graft polymer was formed. After this addition a slight cloudiness of the reaction mixture indicated that graft polymer had formed and the remaining monomer solution was added dropwise over a further three hour period. Polymerisation was continued for a further two hours, to give a viscous, translucent dispersion (conversion 90%, from solids content). The polymer had a molar ratio of the fluorosilane to vinyl methyl ether of 1:1.33. Cyclohexane was removed by centrifugation of the fluoropolymer particle dispersion, followed by washing with ethanol. The centrifuged ethanolic dispersion was then redispersed in glycerol to the desired solids content.

EXAMPLE 8

The following is a further example of a two-part mouthwash composition

|  | % |
|---|---|
| First composition |  |
| Particles of fluoropolymer B | 2.0 |
| KH$_2$PO$_4$ | 0.66 |
| NaOH | 0.11 |
| Water | to 100.0 |
| Second composition |  |
| RETEN 220 | 0.0067 |
| Water | to 100.0 |

One part of the first composition is mixed with three parts of the second composition before use. Particles of the fluoropolymer retained in the mouth slowly hydrolyse to release fluoride ions.

The fluoropolymer B is a poly (methacryloyl fluoride/methyl methacrylate) having an MF/MMA molar ratio of 1:1 which was prepared in the form of the first composition as follows.

A mixture (4.0 g) of equimolar proportions of methacryloyl fluoride and methyl methacrylate was dissolved in dry acetone (20 cc) and azobisisobutyronitrile (0.10 g) added. The solution was purged with nitrogen and the monomer was polymerised under a nitrogen blanket at 60° C. for 12 hours. The resulting polymer was precipitated into dry n-hexane and was dried under nitrogen to give a glassy powder (1.0 g; yield=25%).

A latex of the copolymer was prepared using an inverse phase emulsification technique. The copolymer (3.6 g) was dissolved in a solution of oleic acid (0.4 g) in dichloromethane (36 g). Ammonium hydroxide (0.5 cc "880" ammonia in 36 g water) was added with stirring and a viscosity increase was noted until phase inversion, marked by a sudden drop in viscosity, occurred. The resulting emulsion was then subject to ultrasonic dispersion. The dichloromethane was removed under vacuum at <40° C. to give a stable colloidal latex, which was then diluted with phosphate buffer (pH 7) to the desired solids content. The polymer particle size was varied by changing the ultrasonication time.

EXAMPLE 9

The following first and second compositions are filled, respectively, into the compartments of a two-compartment toothpaste tube adapted to dispense simultaneously equal proportions of the two compositions.

|  | % |
|---|---|
| First Composition |  |
| Particles of MgF$_2$ | 0.33 |
| Hydroxyethylcellulose (Natrosol 250 HR) | 3.00 |
| Sorbitol syrup (70% solution) | 30.00 |
| Disodium hydrogen phosphate | 0.23 |
| Saccharin | 0.10 |
| Non-ionic detergent | 1.50 |
| Flavour | 1.00 |
| Water | to 100.00 |
| Second Composition |  |
| FLOC AID 305 | 0.08 |
| Hydroxyethylcellulose (Natrosol 250 HR) | 3.00 |
| Sorbitol syrup (70% solution) | 30.00 |
| Saccharin | 0.10 |
| Non-ionic detergent | 1.50 |
| Flavour | 1.00 |
| Water | to 100.00 |

Both compositions are adjusted to pH7 with sodium hydroxide.

The compositions may also contain as, desired, colourant and/or preservative. The first composition may be modified by including therein an appropriate amount of a silica abrasive agent to enhance the cleaning action of the dentifrice.

It will be appreciated that while the above examples have been described in relation to the provision in the oral cavity of a reservoir of therapeutically active fluoride ions, particles capable of slowly releasing other therapeutic agents, e.g. an antiplaque agent in microencapsulated form, can also be used.

What we claim is:

1. A method of fluoridating oral fluids which comprises introducing into the oral cavity an oral hygiene product obtained by admixing a first composition and a second composition wherein said first composition comprises a suspension of particles in a medium in which the particles are substantially insoluble which slowly releases fluoride ions in saliva in the mouth for a time greater than about 2 hours, and said second composition comprises an aqueous solution of a cationic polymer, in which method the first and second compositions are admixed in the oral cavity or at the time of usage just prior to introduction into the oral cavity.

2. The method as claimed in claim 1 wherein the particles are particles of a divalent metal fluoride.

3. The method as claimed in claim 1 wherein the particles have a size of 0.01 μm to 5 μm.

4. The method as claimed in claim 2 wherein the particles are particles of magnesium fluoride.

5. The method as claimed in claim 1 wherein the cationic polymer has a cationic charge density of at least 0.0005.

6. The method as claimed in claim 1 wherein the concentration of the cationic polymer in the admixture of the first and second compositions is 3 to 600 ppm.

7. The method as claimed in claim 1 in the form of a mouthwash or dentifrice.

8. The method as claimed in claim 1 wherein one or both of the first and second composition comprises a flavouring agent.

* * * * *